United States Patent [19]

Senftle et al.

[11] Patent Number: 4,617,467
[45] Date of Patent: Oct. 14, 1986

[54] APPARATUS FOR CHARACTERIZING KEROGENS

[75] Inventors: Joseph T. Senftle; Stephen R. Larter, both of Lake Elsinore, Calif.

[73] Assignee: Union Oil Company of California, Los Angeles, Calif.

[21] Appl. No.: 672,395

[22] Filed: Nov. 16, 1984

[51] Int. Cl.$^4$ ............................................. G01N 21/64
[52] U.S. Cl. .............................. 250/461.1; 250/461.2; 350/523
[58] Field of Search ................. 250/253, 458.1, 461.1, 250/461.2; 350/523, 528

[56] References Cited

U.S. PATENT DOCUMENTS

| | | |
|---|---|---|
| 3,637,283 | 1/1972 | Tasaki et al. . |
| 3,971,621 | 7/1976 | Albrecht-Buehler . |
| 4,102,565 | 7/1978 | Takizawa et al. . |
| 4,236,071 | 11/1980 | Chimenti ................ 250/461.1 |
| 4,245,507 | 1/1981 | Samulski . |
| 4,251,128 | 2/1981 | Feinbloom . |
| 4,284,897 | 8/1981 | Sawamura et al. ........... 250/461.2 |
| 4,291,938 | 9/1981 | Wagner . |
| 4,329,015 | 5/1982 | Feinbloom . |
| 4,376,890 | 3/1983 | Engström et al. . |

FOREIGN PATENT DOCUMENTS 237564 9/1945 Switzerland ............... 350/523

*Primary Examiner*—Janice A. Howell
*Attorney, Agent, or Firm*—Dean Sandford; Gregory F. Wirzbicki; Robert J. Baran

[57] ABSTRACT

This invention provides an illuminator adapted to be coupled to a microscope to provide radiation in the ultraviolet region which comprises: (a) a housing having an internal passage way, in optical communication with two windows defined by said housing, said housing being adapted to couple to a microscope body with said windows aligned with the optical axis of the microscope, (b) a mirror located within and extending substantially completely across said internal passageway and adapted to reflect ultraviolet radiation at a first wavelength and transmit radiation at a longer wavelength than said first wavelength, said mirror being centered about said optical axis of the microscope at an angle of about forty-five degrees, (c) a fiber optic cable having a first end coupled with said housing and a second end adapted to receive ultraviolet radiation, said fiber optic cable adapted to introduce ultraviolet radiation into said internal passageway for downward deflection by said mirror along said optical axis of the microscope, and (d) a source of ultraviolet radiation comprising a laser adapted to illuminate said second end of said fiber optical cable.

9 Claims, 4 Drawing Figures

ALTERATION WITH TIME OF FLUORESCENCE

SUCCESSIVE FLUORESCENCE SPECTRA
AFTER VARIOUS PERIODS OF EXCITATION

APPARATUS FOR CHARACTERIZING KEROGENS

BACKGROUND OF THE INVENTION

1. Field of the Invention

The instant invention relates to an apparatus for characterizing a kerogen by measuring the variation, with time, of the fluorescent spectrum thereof. Both the spectral distribution and intensity at certain wavelengths change with the maturity of the kerogen.

2. Background of the Art

An important parameter to predict the potential for oil generation of a source rock is the alteration with time of the fluorescence emission during irradiation at a constant wave length as measured on a polished sample of such source rock. This parameter has been discussed by Teichmiller et al., Erdal v. Kohle, 30, pp. 387–398 and by Leythaeuser et al. Proc. 10th World Petrol. Congr. (Bucarest), 2, pp. 31–41, Heyden, London. Teichmiller reports that a positive alteration occurs in immature source rocks and a negative alteration occurs in mature source rocks when the fluoresence is measured at 546 nanometers. Thus, it is known that the measurement of alteration of fluorescence holds great promise in determining the level of maturity of organic matter within the sediment and its potential as a source of oil (hydrocarbons).

Conventional optical microscopic techniques cannot resolve and describe particles of kerogen smaller than about 1 micrometer. However the characterization of the fluorescence of such small particles would yield important data as to maturity thereof. To this day, however, there is no microscope available which is suitable for providing the necessary data regarding the rapid decay or rapid change of the fluorescent spectra, with time, of such small samples of kerogen.

Various reported improvements in microscopes, that are used for purposes other than characterizing kerogen, have currently come to light. For example, in U.S. Pat. No. 4,329,015, a fiber optic cable is utilized to direct light into the microscope body to increase the amount of light available. The patentee reports that is necessary to tilt the objective lens of his microscope from the optical axis to ensure that spurious light or reflections from the surface of the objective lens do not appear in the visual plane of said microscope. It is clear that if reflectance is occurring, it would decrease to some extent the amount of light available at the eye piece of microscope in relation to the amount of light provided by the fiber optic cable.

In U.S. Pat. No. 4,291,938, fiber optic cables are arranged around in an annular area coaxial with the optical axis of an imaging optical element. This arrangement arguably produces an improved dark field illumination in the microscope. It is noted that the patentee requires a curved objective lens to converge the light emanating from the ends of the optical fibers and thereby focus such light at the focal plane of the microscope. The shape of the lens disclosed in this patent is known to cause reflectance of at least a portion of the light which impinges thereon. Thus, again, the amount of light being provided by the fiber optic cables is greater than the amount available for illuminating a sample in the object plane of this microscope.

In U.S. Pat. No. 3,971,621, a microscope is described which utilizes, as a light conductor, a bundle of glass fibers arranged to provide light, at an angle of from 40° to 50°, at the point at which the the optical axis intersects the objective of the microscope. Thus, this reference also discloses the use of a fiber optic cable in conjunction with a microscope, however, such use is to generate relief-like contrast of the microscopic images, only.

U.S. Pat. No. 4,120,565, discloses a microscope for investigating the eye, which includes an optical guide in the form of a glass element. The optical guide is illuminated at one end by a lamp and the radiation from the lamp is carried by the guide to provide uniform illumination around the eye that is being investigated.

Thus is clear that the use of fiber optics in the microscopes of the prior art, have been limited to illumination from the well-known lamps of the prior art.

It is thus one object of this invention to provide an apparatus for characterizing kerogens by analyzing the fluorescence thereof.

It is another object of this invention to provide an an illuminator for coupling an ultraviolet laser with a microscope.

It is another object of the invention to provide an illuminator wherein substantially all of the incoming ultraviolet radiation is utilized for irradiating a kerogen and substantially all of the fluorescent radiation is utilized for analyzing the fluorescence spectrum thereof.

Other objects and advantages of the instant invention will become apparent from a careful reading of the specification below.

SUMMARY OF THE INVENTION

The instant invention provides an illuminator adapted to be coupled to a microscope to provide radiation in the ultraviolet region which comprises: (a) a housing having an internal passage way in optical communication with two windows defined by said housing, said housing being adapted to couple to a microscope body with said windows aligned with the optical axis of the microscope, (b) a mirror located within and extending substantially completely across said internal passageway and adapted to reflect ultraviolet radiation at a first wavelength and transmit radiation at a longer wavelength than said first wavelength, said mirror being positioned to intersect said optical axis of the microscope at an angle of about forty-five degrees, (c) a fiber optic cable having a first end coupled with said housing and a second end adapted to receive ultraviolet radiation, said fiber optic cable being adapted to introduce ultraviolet radiation into said internal passageway for downward deflection by said mirror along said optical axis of the microscope, and (d) a source of ultraviolet radiation comprising a laser adapted to illuminate said second end of said fiber optic cable.

The mirror extending substantially completely across said internal passageway ensures that a maximum of the ultraviolet radiation entering the housing is available for exciting kerogen in the sample and causing it to fluoresce, i.e. emit radiation at a wavelength higher than said first wave length.

This illuminator is useful in a method for characterizing kerogens which comprises (a) irradiating a sample comprising said kerogens with ultraviolet radiation to cause said kerogens to emit fluorescent radiation (b) separating said fluorescent radiation into a spectrum of individual wave lengths and (c) measuring the change in intensity of said individual wave lengths with time. This method is conveniently carried out by a system for analyzing the fluorescence spectra of kerogens irradiated with ultraviolet radiation which comprises (a) a microscope including a microscope body disposed about a central axis defining an optical axis, an objective lens positioned within said body and aligned about said axis, and an eyepiece lens assembly disposed about said axis and adapted for viewing a sample comprising kerogen positioned at an object plan located beneath said objective lens, (b) a source of ultraviolet radiation comprising said illuminator wherein said ultraviolet laser is optically coupled with said microscope by means of a fiber optic cable and adapted to introduce ultraviolet radiation in a downward direction along said optical axis, to thereby irradiate said sample and cause said kerogen to emit fluorescent radiation, (c) a prism or diffraction grating adapted to separate said fluorescent radiation into a spectrum of individual wave lengths, and (d) a photo diode array coupled directly with a multi-channel analyzer to measure the change in intensity of said individual wave lengths with time.

BRIEF DESCRIPTION OF THE DRAWING FIGURES

FIG. 1 schematically illustrates a system which may utilize the illuminator of this invention for analyzing the fluorescent spectra of kerogens irradiated with ultraviolet radiation;

DETAILED DESCRIPTION OF THE INVENTION

Figure 1:
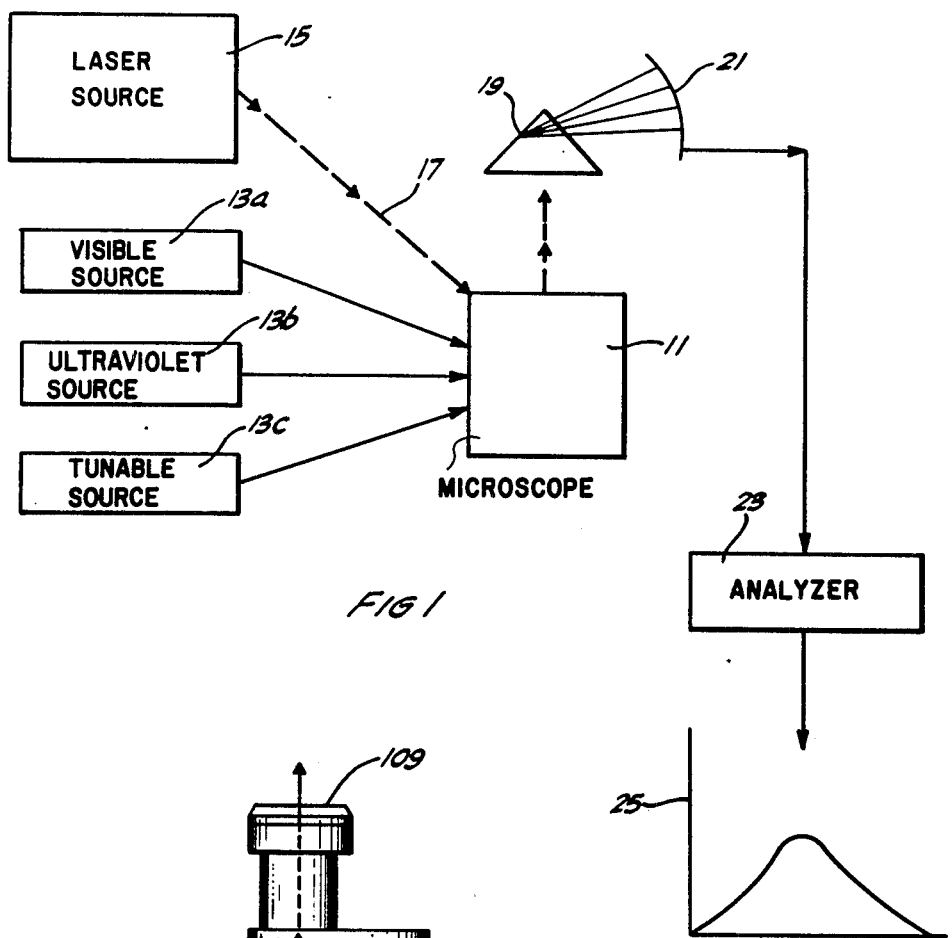

The invention may be more clearly understood by reference to FIG. 1, which describes a novel system for analyzing the emission or fluorescence spectrum of a kerogen sample irradiated by ultraviolet radiation from a laser source to determine the change of such spectrum with time.

In FIG. 1, a microscope 11, is shown to be optically coupled to various radiation sources. 13a is a halogen lamp which is useful for providing visible radiation whereby a sample placed for viewing by the microscope, may be visually examined by focusing on specific areas of interest, i.e., kerogen or whole sediment. Upon identifying an area of interest in the sample, a source of ultraviolet radiation, such as a mercury vapor lamp 13b, which, with appropriate filter combinations, provides ultraviolet radiation having a maximum intensity at about 365 nanometers, may be energized to irradiate the area of interest and determine if such portion has fluorescent characteristics. Alternatively, or in addition thereto, the area of interest may be irradiated with a radiation source 13c which is tunable over the ultraviolet region, ranging from 300 to 700 nanometers. A suitable tunable radiation source, might be a xenon light source, optically coupled with a monochronomator which may be tuned to provide a specific wavelength in the ultraviolet region between 300 and 700 nanometers. Light sources 13a, 13b and 13c may be coupled with the microscope, using the conventional lateral entry at the back of such microscope or by other means known in the art.

A replacement for the aforesaid conventional radiation source is an ultraviolet laser source 15 which may be coupled to the microscope by means of a fiber optic cable 17. The ultraviolet laser source, together with said fiber optic cable and the cartridge, which are further described below, comprise the illuminator of this invention. When a sample has been determined to be of interest, the conventional radiation sources may be removed and replaced with the illuminator described below to enable the microscope operator to irradiate the area of interest with ultraviolet radiation of a specific wavelength provided by the ultraviolet laser. Suitably a helium-cadmium or a nitrogen laser is coupled to the microscope by means of the fiber optic cable.

Upon irradiation of the sample with the ultraviolet laser, fluorescence occurs and the fluorescent radiation emanating from the sample is passed through a prism or a diffraction grating 19 to separate said fluorescent radiation into its individual components, i.e., into a spectrum of individual wavelengths comprising said emission or fluorescent radiation. The change in intensity of the individual wavelengths comprising said spectrum, with time, is measured as further described below.

The individual wavelengths preferably will be directed to impinge on a photo diode array 21, which serves as means to amplify the intensity of individual wavelengths for accurate analysis. The signal emanating from said photodiode array is sent through a multichannel analyzer 23 which converts the individual signals into a spectrum, as illustrated at 25. The spectrum is measured over a time period of 1 to 1000 seconds, at intervals of 5 to 10 milliseconds or less. The change in the intensity of the individual wave lengths of radiation comprising said spectrum, with time, is monitored to determine the characteristics of the kerogen sample being analyzed.

Figure 2:
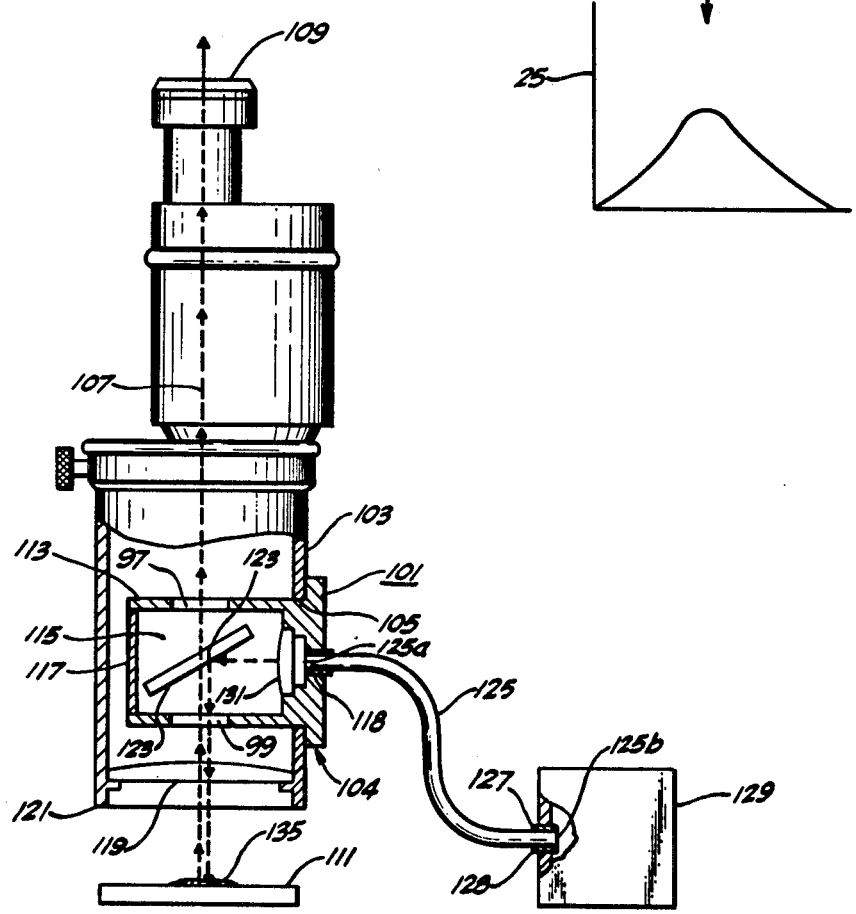
FIG. 2 is a schematic side view of a microscope utilizing the illuminator of this invention.

In FIG. 2, a microscope, including the novel illuminator, and suitable for use in the above system, is described. The illuminator comprises an ultraviolet laser 129, a fiber optic cable, 125, and a cartridge 101 which fits into the microscope in place of the optical system utilized in the conventional light sources for a microscope.

The illuminator, as shown, is adapted to be coupled to a microscope body 103, by insertion of cartridge 101 through a port 105, provided in the microscope body, for the purpose of providing radiation in the ultraviolet region. The microscope includes microscope body 103 disposed about a central axis 107, defining an optical axis. The microscope has an eye piece lens assembly 109, which is disposed about said central axis and adapted for viewing a sample, positioned at object plane 111, located below the microscope.

The microscope also includes an objective lens 119, within said microscope body and intersecting the central axis thereof. As shown, the objective lens is, preferably, at the lower end 121 of said housing.

The illuminator comprises a cylindrical housing 113, defining an internal passageway 115, which intersects said central axis 107, when the cartridge is inserted into the microscope body. The cartridge also comprises a flanged top 104, defining a stepped aperture 118, which top is affixed to the cylindrical housing and sized to prevent said cylindrical housing from passing completely into the microscope body. A mirror 123 is located within said housing and extends substantially completely across the internal passageway to intersect the central axis an angle of about 45°. The mirror is a dichroic mirror which is adapted to completely reflect the incoming ultraviolet radiation and completely transmit the fluorescent radiation. The cartridge also includes windows 97 and 99 which are defined by said cylindrical housing and also intersect said central axis to transmit both the incoming and fluorescent radiation. As shown, the windows are in optical communication with said internal passageway.

A fiber optic cable 125, having a first end 125a, is coupled with said cartridge through fitting 127, which may be press fit into said stepped aperture 118. The second end 125b, of said fiber optic cable, is coupled to an ultraviolet laser source 129. As shown, end 125a is mechanically held in optical communication with said mirror 123, by fitting 127, which secures said fiber optic cable to said housing in the correct optical alignment. The fiber optic cable is also mechanically secured to laser source 129 by means of a sleeve 128. Preferably, the fiber optic cable comprises a plurality of optical fibers which are assembled to provide the fiber optic cable. In operation, end 125b of the fiber optic cable is illuminated by ultraviolet laser source to provide narrow wavelength radiation which travels along fiber optic cable 125 and enters the housing through quartz converging lens 131. The converging lens, as shown, is affixed about said stepped aperture 118 and adapted to converge any random or spurious rays emanating from end 125a and focus the radiation on mirror 123, at approximately the point at which said mirror intersects the optical axis. The ultraviolet radiation is directed downward, along the optical axis, by mirror 123, through objective lens 119, to irradiate sample 135.

The sample has previously been adjusted by the above described techniques to align an area of interest, i.e. a kerogen moiety in the sample, with the optical axis of the microscope. The sample is illuminated and fluoresces to provide a spectrum which is characteristic of the kerogen in the sample. Fluorescent radiation having a wavelength longer than the wavelength of the exciting laser ultraviolet radiation is emitted back along the optical axis and through the mirror to the prism or diffraction grating previously described.

In the illuminator of this invention, the placement of the mirror substantially completely across the passageway of the housing ensures that all of the light which is generated by the ultraviolet laser is utilized for illumination of the sample. Moreover, all of the fluorescent radiation is passed through the mirror and used to characterize the fluorescence spectrum. The orientation of the objective lens, perpendicular to the optical axis, further ensures that no radiation from the ultraviolet laser source or fluorescent radiation is lost by reflection.

The following example illustrates a specific method for characterizing the fluorscence spectrum of a kerogen sample by use of the microscope, including the illuminator, and the system described above. These examples, however, are not to be construed as limiting the scope of the invention which is defined by the appended claims.

EXAMPLE

Figure 3:
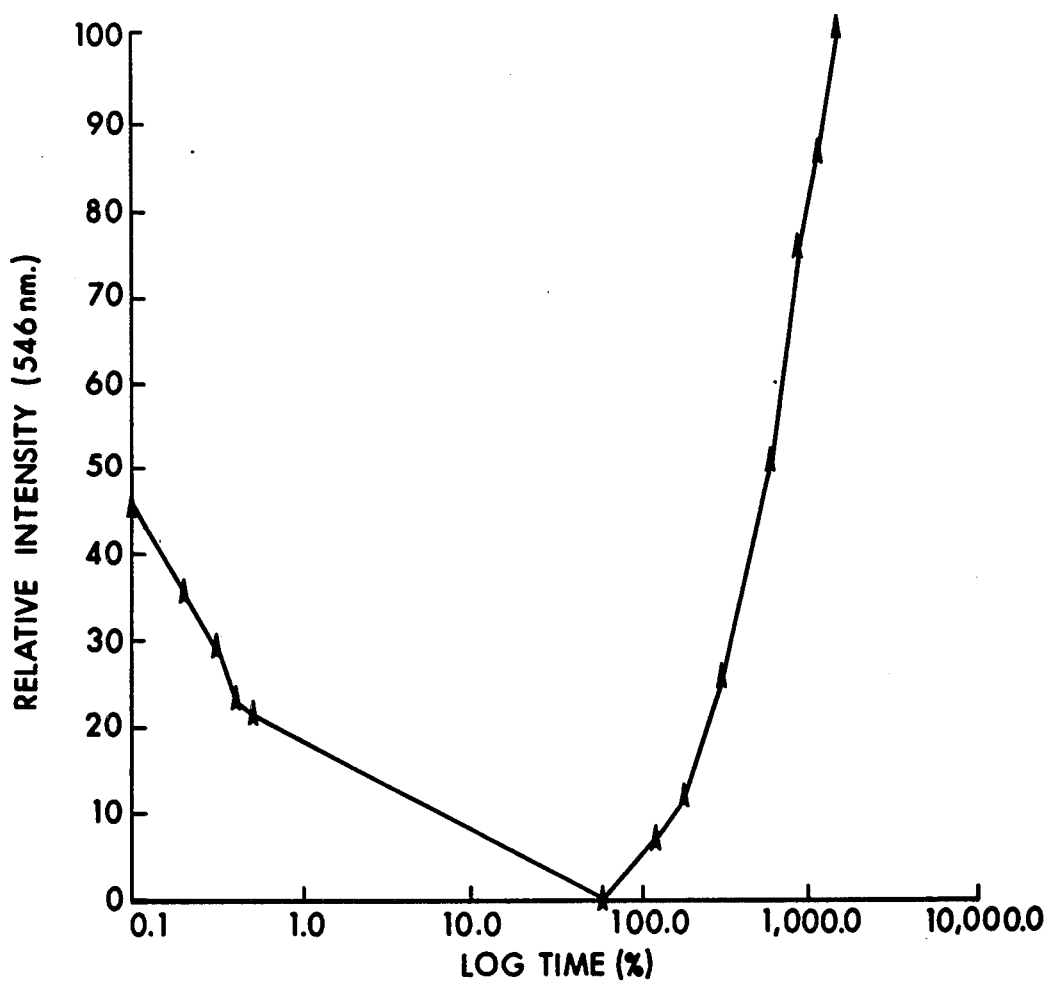
FIG. 3 shows the change in the intensity of flurorescence spectrum a kerogen sample, coorongite, with time, at 546 nanometers (nm)
Figure 4:
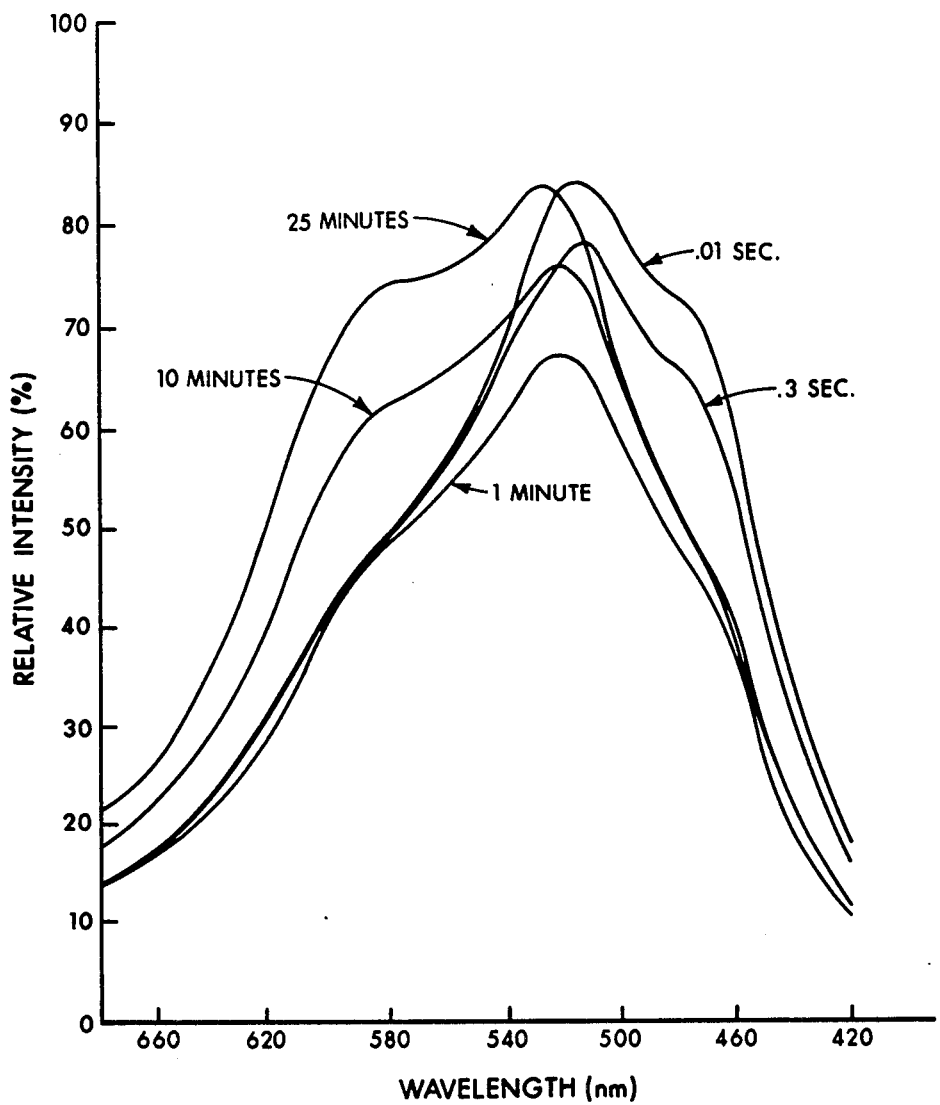
FIG. 4 shows the change in the intensity of fluorescence of the same kerogen sample with time, over the range of 420 to 680 nm.

Using the system of FIG. 1 and the microscope, including the illuminator of FIG. 2, a sample of coorongite, from Australia, is analyzed and fluorescence spectra of FIG. 4 is obtained. Coorongite is derived from *Botyococcus braunii* and is believed to be an intermediate stage in the formation of torbanite, a form of algal-rich coal derived from algae. The alteration of said fluorescence spectrum with time is obtained by measurement of said spectrum at 0.01 seconds, 0.3 seconds, 1 minute, 10 minutes, and 25 minutes. Within the first minute, the spectrum generally does not shift but decreases in intensity (negative alteration). After a minute of excitation, there is a spectral shift to higher wavelengths along with an increase in intensity of fluorescence (positive alteration). This particular alteration with time is determined to be characteristic of coorongite and therefore it may be distinguished from ther exinite macerals In contrast, when the fluorescence of the same sample is measured at 546 nm, as shown in FIG. 3, the change in intensity of fluorescence, with time, at 546 nm, does not distinguish the coorongite sample from other exinite macerals which may not be as promising from the standpoint of indicating a hydrocarbon source.

The illuminator of this system of this invention may also be utilized in a method to distinguish cooronite from the other alginites or marine algae, e.g. kukersite, tasmanite, torbanite. Moreover, the illuminator of this system may be used to distinguish the above alginites from other exinite macerals such as sporinite, cutinite and resinite. This ability to distinguish exinite macerals originating from marine algae (such as the above alginites) from exitinite macerals originating from terrestial algae (such as resinite) is desirable since the source potential of alginite is different from that of resinite.

While particular embodiments of the invention have been described, it will be understood, of course, that the invention is not limited thereto since many obvious modifications can be made, and it is intended to include within this invention any such modification as will fall within the scope of the appended claims.

What is claimed is:

1. An illuminator adapted to be coupled to a microscope to provide radiation in the ultraviolet region which comprises:
    (a) a housing having an internal passage way, in optical communication with two windows defined by said housing, said housing being adapted to couple to a microscope body with said windows aligned with the optical axis of the microscope,
    (b) a mirror located within and extending substantially completely across said internal passageway and adapted to reflect ultraviolet radiation at a first wavelength and transmit radiation at a longer wavelength than said first wavelength, said mirror being positioned to intersect said optical axis of the microscope at an angle of about forty five degrees,
    (c) a fiber optic cable having a first end coupled with said housing and a second end adapted to receive ultraviolet radiation, said fiber optic cable being adapted to introduce ultraviolet radiation into said internal passageway for downward deflection by said mirror along said optical axis of the microscope, and
    (d) a source of ultraviolet radiation comprising a laser adapted to illuminate said second end of said fiber optic cable.

2. The illuminator of claim 1 further including a lens mounted within said internal passageway and adapted to converge said ultraviolet radiation at the intersection of said mirror and said optical axis of the microscope.

3. The illuminator of claim 1 wherein said laser comprises a helium-cadmium laser or a nitrogen laser.

4. The illuminator of claim 2 further including a flanged top affixed to the housing and sized to prevent said housing from passing completely into said microscope body, said flanged top defining a stepped aperture to provide a smaller and larger opening in said housing and said first end of said fiber optic cable being press fit into said smaller opening and said lens being mounted about said larger opening.

5. The illuminator of claim 2 wherein said housing is a cylindrical housing.

6. The illuminator of claim 2 wherein said fiber optic cable comprises a plurality of optical fibers.

7. A microscope comprising the illuminator of claim 1.

8. A microscope including a microscope body disposed about a central axis defining an optical axis, an objective lens positioned within said body and aligned about said axis, and an eyepiece lens assembly disposed about said axis and adapted for viewing a sample comprising kerogen positioned at an object plan located beneath said objective lens, and a source of ultraviolet radiation comprising said illuminator of claim 1.

9. A system for analyzing the fluorescence spectrum of a kerogen irradiated with ultraviolet radiation which comprises (a) a microscope including a microscope body disposed about a central axis defining an optical axis, an objective lens positioned within said body and aligned about said axis, and an eyepiece lens assembly disposed about said axis and adapted for viewing a sample comprising said kerogen positioned at an object plane located beneath said objective lens, (b) a source of ultraviolet radiation comprising said illuminator of claim 1 adapted to irradiate said sample and cause said kerogen to emit a fluorescent radiation, (c) a prism or diffraction grating adapted to separate said fluorescent radiation into a spectrum of individual wave lengths, and (d) a photo diode array coupled directly to a multichannel analyzer to measure the change in intensity of radiation at said individual wave lengths with time.

* * * * *